United States Patent
Langen et al.

[11] Patent Number: 6,013,428
[45] Date of Patent: Jan. 11, 2000

[54] COLOR PHOTOGRAPHIC RECORDING MATERIAL HAVING A 2-EQUIVALENT MAGENTA COUPLER AND A WHITE COUPLER

[75] Inventors: Hans Langen, Bonn; Heinrich Odenwälder, Leverkusen; Uwe Dahlhaus, Burscheid, all of Germany

[73] Assignee: Agfa-Gevaert AG, Leverkusen, Germany

[21] Appl. No.: 08/891,391

[22] Filed: Jul. 11, 1997

[30] Foreign Application Priority Data

Jul. 19, 1996 [DE] Germany ............................... 19629142

[51] Int. Cl.⁷ .............................. G03C 7/30; G03C 7/333
[52] U.S. Cl. .......................... 430/551; 430/555; 430/556; 430/565
[58] Field of Search ........................ 430/551, 555, 430/554, 556, 565, 214

[56] References Cited

U.S. PATENT DOCUMENTS 5,478,712 12/1995 Singer et al. ............................ 430/551
5,601,968 2/1997 Weber et al. ............................ 430/551

FOREIGN PATENT DOCUMENTS 914145 12/1962 Spain .

*Primary Examiner*—Richard L. Schilling
*Assistant Examiner*—Amanda C. Walke
*Attorney, Agent, or Firm*—Connolly Bove Lodge & Hutz LLP

[57] ABSTRACT

A colour photographic recording material having at least one red-sensitive silver halide emulsion layer which is associated with a cyan coupler, at least one green-sensitive silver halide emulsion layer which is associated with a magenta coupler, at least one blue-sensitive silver halide emulsion layer which is associated with a yellow coupler contains in at least one green-sensitive silver halide emulsion layer a 2-equivalent pyrazolone coupler and in a photosensitive or non-photosensitive layer a white coupler of the formula (I)

(I)

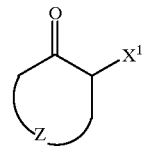

in which $X^1$ means an acyl residue derived from an aliphatic, cycloaliphatic or aromatic carboxylic or sulphonic acid, a carbonic acid semi-ester or a carbamic acid, Z means the residue required to complete a saturated or partially unsaturated 5- or 6-membered carbocyclic ring which is optionally substituted and/or provided with a further fused ring or ring system.

The colour images produced using the recording material exhibit elevated storage stability without a subsequent increase in fog or a subsequent increase in colour density or spotting occurring during storage.

10 Claims, No Drawings

COLOR PHOTOGRAPHIC RECORDING MATERIAL HAVING A 2-EQUIVALENT MAGENTA COUPLER AND A WHITE COUPLER

This invention relates to a colour photographic recording material having silver halide emulsion layers of differing spectral sensitivity which contains, associated with a green-sensitive silver halide emulsion layer, a 2-equivalent pyrazolone coupler and, in a photosensitive or non-photosensitive layer, a white coupler.

2-equivalent pyrazolone couplers have advantages in many respects in comparison with the corresponding 4-equivalent couplers. They require a smaller quantity of silver halide for colour formation, so allowing thinner layers to be produced. They are more resistant to formalin and they have a lesser tendency to yellow as residual couplers present in the layer after processing. Increased development fog is, however, a disadvantage.

The increased development fog observed when 2-equivalent couplers are used may in some cases be suppressed if the 2-equivalent couplers concerned are used in combination with white couplers (DE-B-1 155 675, DE-A-24 20 067, DE-A-39 13 404). However, the combined use of 2-equivalent pyrazolone couplers with 4-alkylpyrazolone type white couplers results in impaired image stability which is discernible after completion of development from an increase in fog and maximum density and is probably attributable to recoupling between the coupled white coupler and the (uncoupled) 2-equivalent pyrazolone coupler still present.

The object of the invention is to provide novel white couplers having a coupling product produced on reaction with the colour developer oxidation product (DOP) which is more stable and has no tendency to recouple with any 2-equivalent pyrazolone coupler still present in the layer.

The present invention provides a colour photographic recording material having at least one red-sensitive silver halide emulsion layer which is associated with a cyan coupler, at least one green-sensitive silver halide emulsion layer which is associated with a magenta coupler, at least one blue-sensitive silver halide emulsion layer which is associated with a yellow coupler and optionally further non-photosensitive layers, characterised in that at least one green-sensitive silver halide emulsion layer contains a 2-equivalent pyrazolone coupler and that at least one photosensitive or non-photosensitive layer contains a compound of the formula (I) (white coupler)

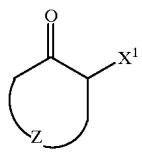

(I)

in which
  $X^1$ means an acyl residue derived from an aliphatic, cycloaliphatic or aromatic carboxylic or sulphonic acid, a carbonic acid semi-ester or a carbamic acid,
  Z means the residue required to complete a saturated or partially unsaturated 5- or 6-membered carbocyclic ring which is optionally substituted and/or provided with a further fused ring or ring system.

An acyl residue represented by X is, for example, a residue of the formulae $-CO-R^{11}$, $-COOR^{11}$, $-CONH-R^{11}$, $-CONR^{11}-R^{12}$ and $-SO_2-R^{11}$, in which $R^{11}$ denotes alkyl, cycloalkyl, aryl or hetaryl and $R^{12}$ denotes a residue as $R^{11}$.

An alkyl group represented by $R^{11}$ or contained in $R^{11}$ is linear or branched, contains, for example, up to 20 C atoms and may optionally be substituted, for example with alkoxy, aroxy or alkoxycarbonyl. Examples of such alkyl groups are methyl, ethyl, propyl, butyl, hexyl, octyl, $-H_{12}H_{25}$, $-C_{13}H_{27}$, $-Cl_4H_{29}$, $-C_{16}H_{33}$, $-C_{18}H_{37}$, $\omega$-(2,4-di-t.-amylphenoxybutyl), $\alpha$-dodecyloxycarbonylethyl.

A cycloalkyl group represented by $R^{11}$ or contained in $R^{11}$ is, for example, cyclopentyl or cyclohexyl.

An aryl group represented by $R^{11}$ or contained in $R^{11}$ is in particular phenyl or substituted phenyl, for example phenyl substituted with halogen (chlorine), alkyl, cycloalkyl, alkoxy, aroxy, sulphamoyl, acylsulphamoyl and/or alkoxycarbonyl.

A hetaryl group represented by $R^{11}$ or contained in $R^{11}$ is, for example, furyl, thienyl, pyridyl or 1,2,4-triazoloyl. Such rings may be further substituted, for example with alkyl or alkylthio.

A carbocyclic ring completed by Z is, for example, a cyclopentane or cyclohexane ring or the relevant ring in an indane, tetralin or dihydroacenaphthene ring system.

In a preferred embodiment, X denotes a group of the formula $-CONH-R^{11}$ with $R^{11}$ having the above-stated meanings.

Suitable examples of compounds of the formula I are shown below:

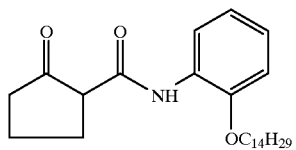

I-1

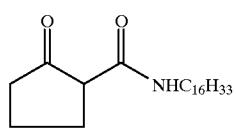

I-2

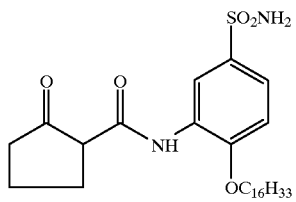

I-3

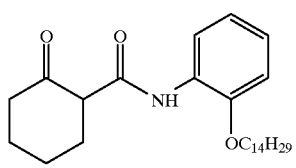

I-4

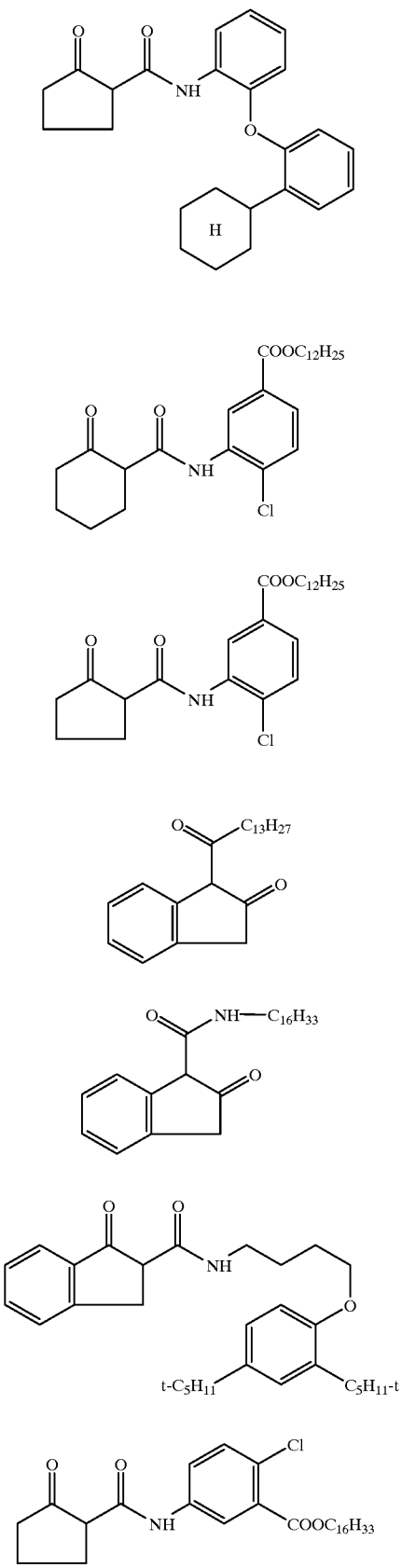
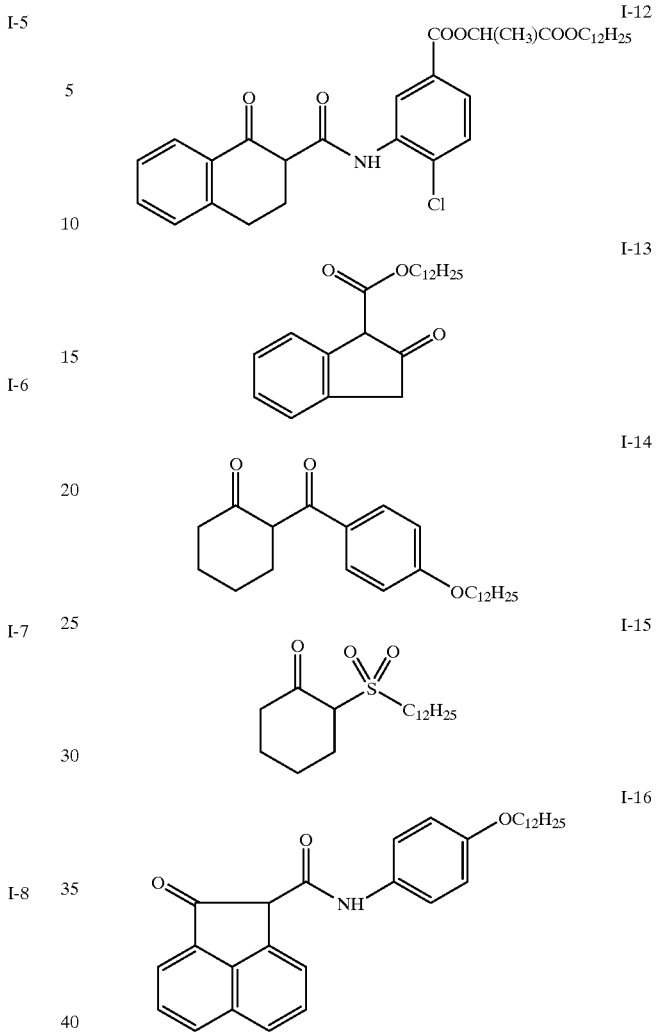

The compounds of the formula I used according to the invention may be produced simply and at low cost. Compounds I-1 to I-7, I-10 to I-12 and I-16 are obtainable by aminolysis of the corresponding β-keto ester with an amine or imine, preferably with the addition of a basic compound, such as for example triethylamine or sodium methylate, at elevated temperature in an inert solvent with the alcohol component of the keto ester used being removed by distillation.

A suitable alternative method is also to convert a cyclic ketone into the enamine thereof, for example the morpholinocyclohexene, acylating this with an acid chloride or an isocyanate and converting the resultant enaminoacyl product into the keto acyl compound under acidic reaction conditions. Such processes are known from the literature. Compounds I-8, I-9, I-13 and I-14 are best produced in this manner.

Compound I-15 is also obtainable via the cyclohexanone enamine by sulphenylation, hydrolysis to yield the ketone and oxidation to yield the sulphone using known methods.

Production of compound I-7

169.8 g of 3-amino-4-chlorobenzoic acid dodecyl ester and 91.1 ml of 2-cyclopentanone carboxylic acid ethyl ester (90%) in 500 ml of xylene are combined with 5 ml of triethylamine.

The mixture is heated to boiling and 300 ml are distilled off within 4 hours at an internal temperature of 140 to 148° C. The residual solvent is then removed by vacuum distillation.

1000 ml of methanol, 20 g of bleaching earth and 5 ml of glacial acetic acid are added to the residue, heating to boiling, the solution filtered off and the filtrate allowed to cool with stirring. Once separated, the crystallisate is washed with 500 ml of methanol and dried to constant weight.

178 g (79.1% of theoretical) of compound 4 are obtained. Melting point: 68.5 to 69.5° C. NMR spectrum corresponds to structure.

The compounds according to the invention are conveniently used in the layers of the photographic recording material in a concentration of 20 to 1000 mg/m², preferably of 50 to 400 mg/M². They are generally added as an emulsion. To this end, the compounds are emulsified, for example, in dissolved form in water or an aqueous gelatine solution and added to the casting solutions. In the case of casting solutions which contain silver halide, addition is conveniently made after sensitisation and stabilisation.

The 2-equivalent pyrazolone couplers used according to the invention are of the formula II

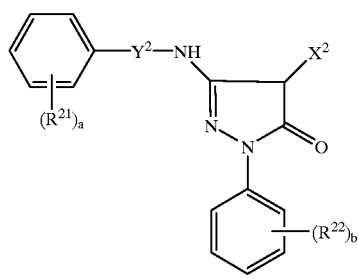

in which $R^{21}$ means fluorine, chlorine, bromine, cyano, —NO₂, —CF₃, alkyl, aryl, acyl, silyl, alkoxy, acylamino, sulphonamido, alkylsulphonyl or arylsulphonyl;

$R^{22}$ means fluorine, chlorine, bromine, cyano, —NO₂, —CF₃, alkyl, acyl, alkoxy, acylamino, sulphonamido, alkylsulphonyl, arylsulphonyl, alkoxysulphonyl or aryloxysulphonyl;

$X^2$ means a leaving group;

$Y^2$ means a single chemical bond or —CO—;

a and b (mutually independently): mean 0 (zero) or an integer from 1 to 5, wherein if a or b is >1, the substituents $R^{21}$ or $R^{22}$ are identical or different.

In a preferred embodiment of the invention, the 2-equivalent pyrazolone coupler is of the formula III

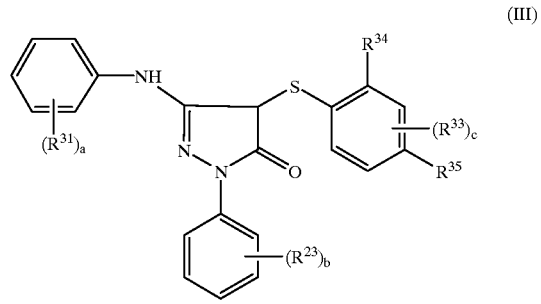

in which $R^{31}$ means a residue as $R^{21}$;

$R^{32}$ means a residue as $R^{22}$;

$R^{33}$ means fluorine, chlorine, bromine, cyano, alkyl, aryl, acyl, silyl, alkylsulphonyl or arylsulphonyl;

$R^{34}$ and $R^{35}$ mean hydrogen, cyano, alkyl, alkoxy, acylamino, sulphonamido, alkoxycarbonyl, alkylsulphonyl, arylsulphonyl, alkoxysulphonyl or aryloxysulphonyl, providing that either $R^{34}$ or $R^{35}$ denotes hydrogen;

a and b (mutually independently): mean 0 (zero) or an integer from 1 to 5, wherein if a or b is >1, substituents $R^{31}$ or $R^{32}$ are identical or different;

c means 0 (zero) or an integer from I to 4, wherein two or more substituents $R^{33}$ are identical or different.

Within the formula III, preferred 2-equivalent pyrazolone couplers are those in which $R^{34}$ means hydrogen and $R^{35}$ means acylamino or sulphonamido, one of the residues $R^{30}$ is in ortho position relative to the NH group and means fluorine, chlorine, bromine or alkoxy and b denotes an integer from 3 to 5.

Very particularly preferred 2-equivalent pyrazolone couplers are of the formula IV

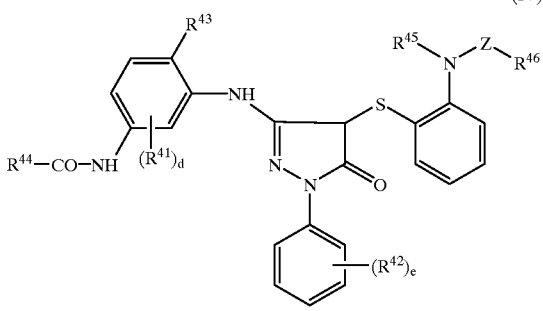

in which $R^{41}$ means a residue as $R^{21}$;

$R^{42}$ means a residue as $R^{22}$;

$R^{43}$ means chlorine or alkoxy;

$R^{44}$ means alkyl or alkoxy;

$R^{45}$ means hydrogen, alkyl or aryl;

$R^{46}$ means alkyl or aryl;

$Z^4$ means —CO— or —SO₂—;

d means 0 or 1; and e means an integer from 3 to 5, wherein two or more substituents $R^{42}$ are identical or different.

In the formulae II, III and IV, an acyl residue represented by $R^{21}$, $R^{22}$ or $R^{33}$ and the acyl residue of an acylamino group represented by $R^{21}$, $R^{22}$, $R^{34}$ or $R^{35}$ are derived from an aliphatic carboxylic acid, a carbamic acid or a carbonic acid semiester.

Examples of suitable 2-equivalent pyrazolone couplers (of the formulae II, III and IV) are shown below.

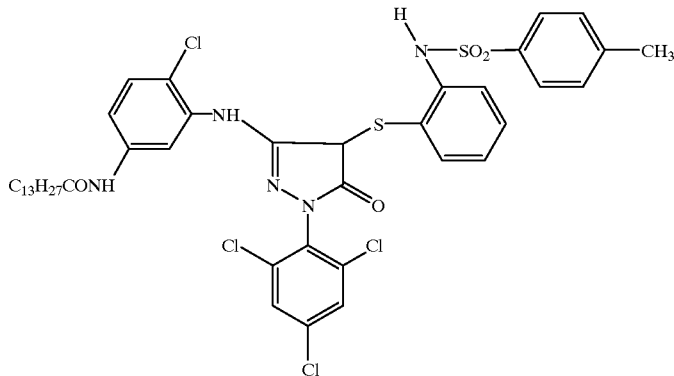

M-1

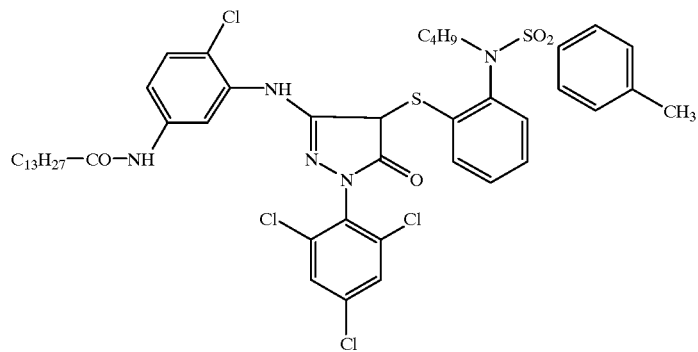

M-2

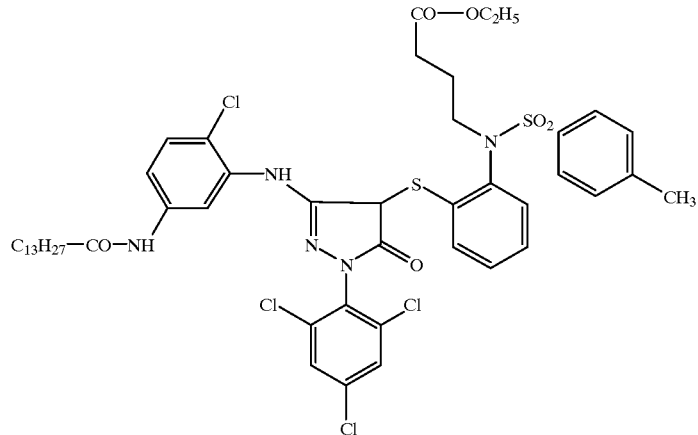

M-3

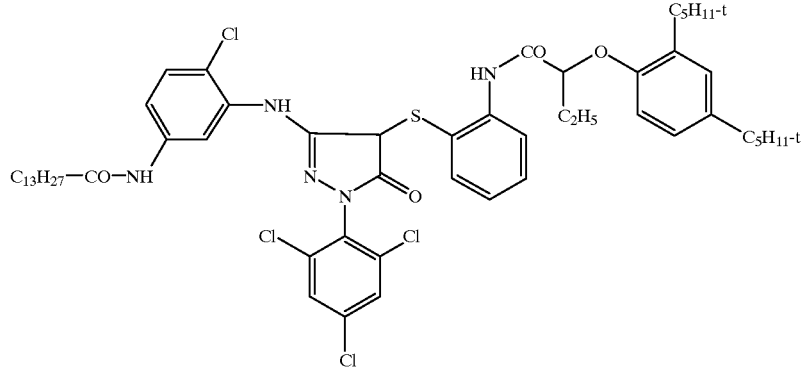
M-4
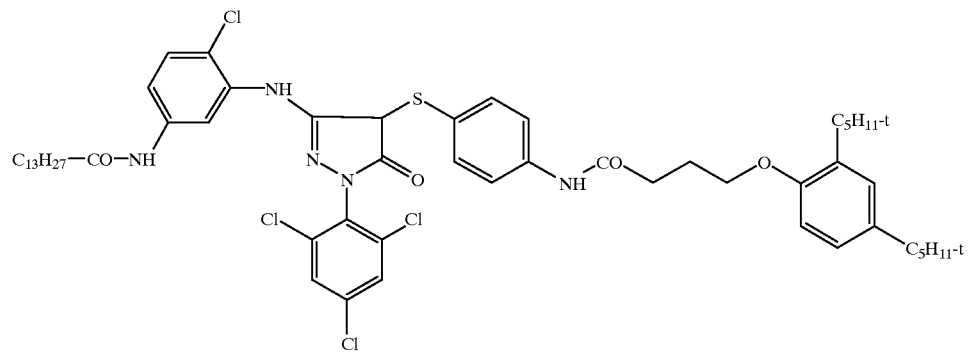
M-5
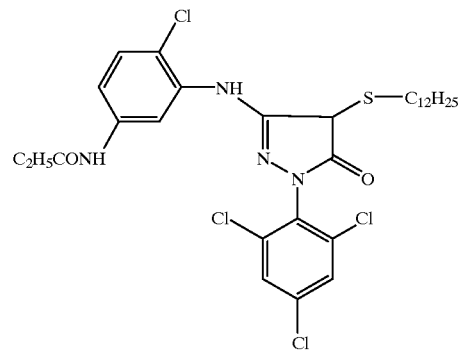
M-6
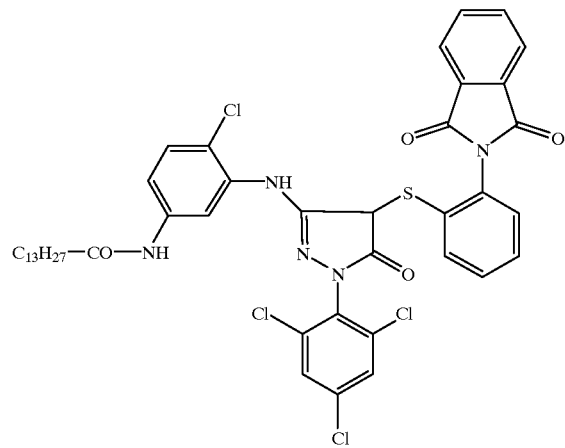
M-7

-continued
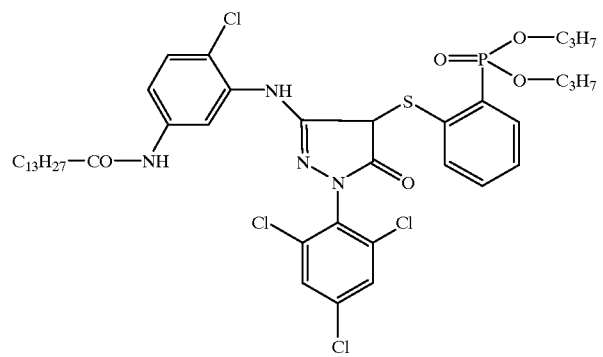
M-8
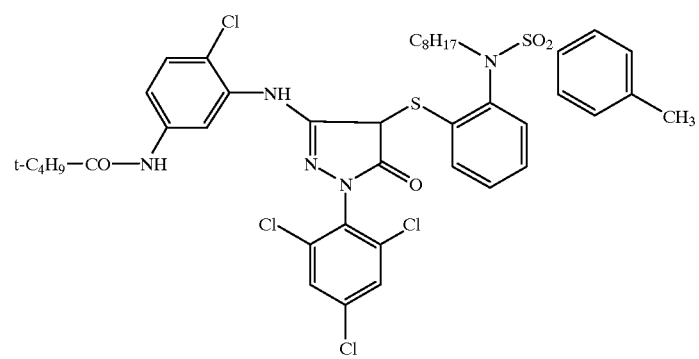
M-9
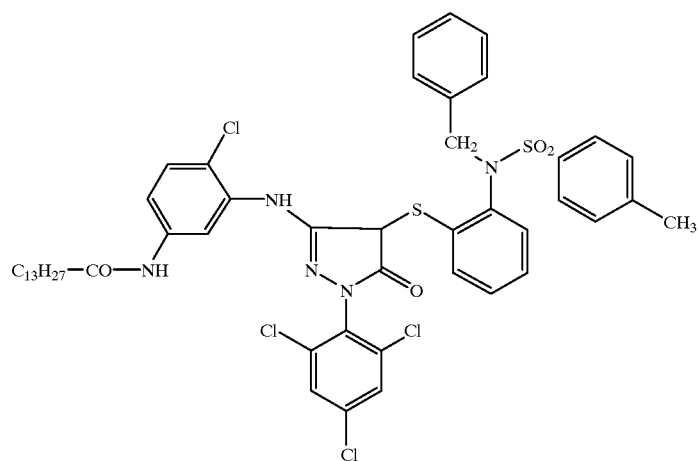
M-10
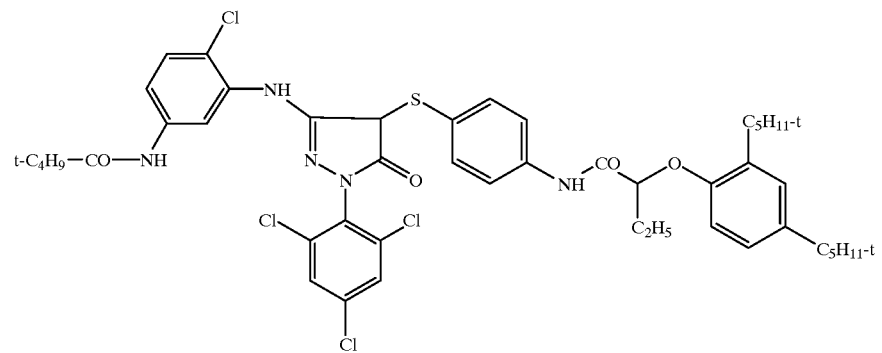
M-11

M-12
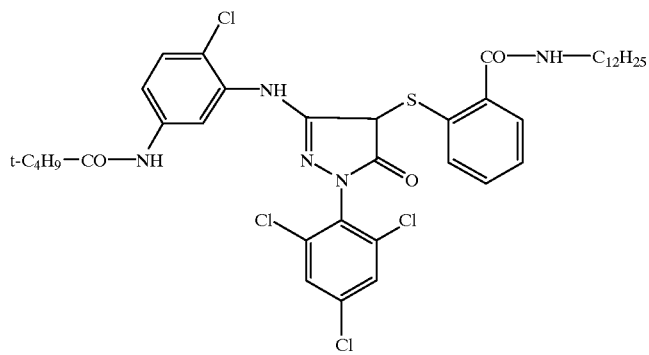
M-13
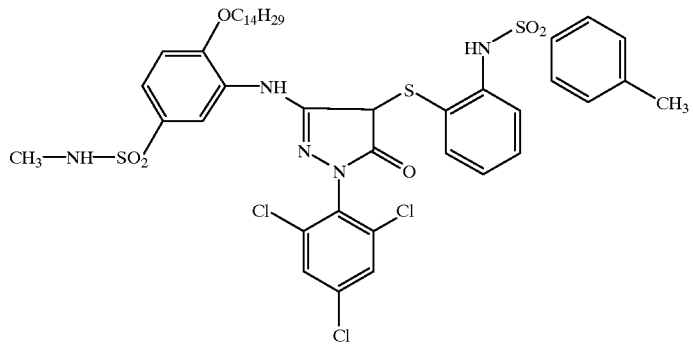
M-14
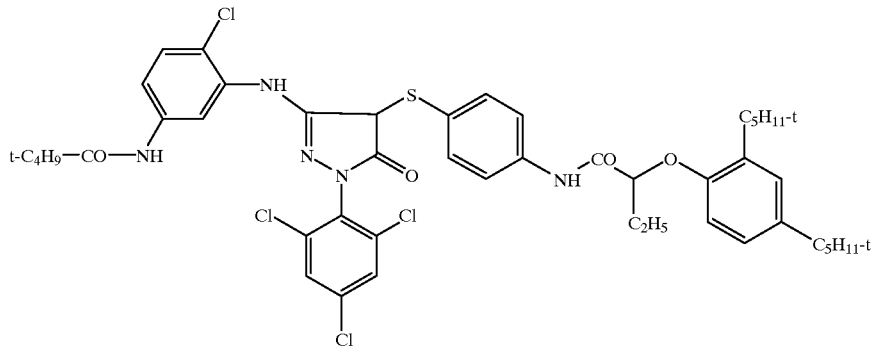
M-15
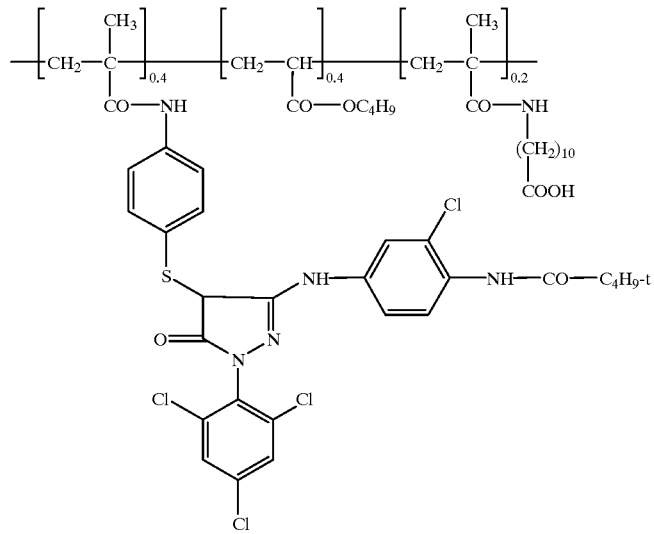

-continued

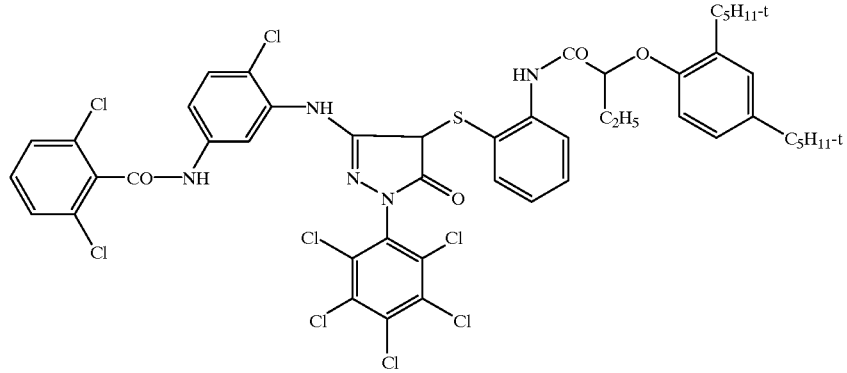

M-16

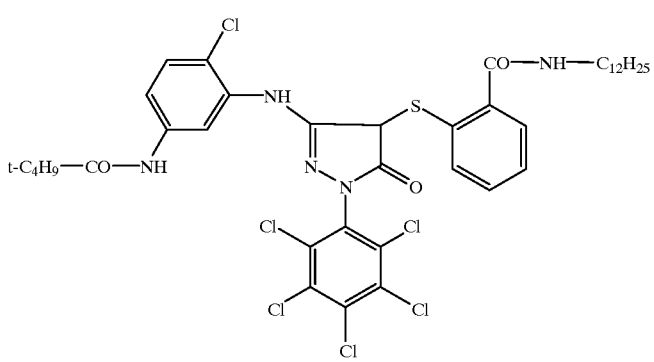

M-17

Examples of colour photographic materials are colour negative films, colour reversal films, colour positive films and colour photographic paper.

The photographic materials consist of a support onto which at least one photosensitive silver halide emulsion layer is applied. Thin films and sheets are in particular suitable as supports. A review of support materials and the auxiliary layers applied to the front and reverse sides of which is given in Research Disclosure 37254, part 1 (1995), page 285.

The colour photographic materials conventionally contain at least one red-sensitive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive partial layers are generally arranged closer to the support than the more highly sensitive partial layers.

A yellow filter layer is conventionally arranged between the green-sensitive and blue-sensitive layers so preventing blue light from reaching the underlying layers.

Possible options for different layer arrangements and the effects thereof on photographic properties are described in J. Inf. Rec. Mats., 1994, volume 22, pages 183–193.

Colour photographic paper, which is usually substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together in another package of layers in order to increase sensitivity (DE-25 30 645).

The substantial constituents of the photographic emulsion layers are binder, silver halide grains and colour couplers.

Details of suitable binders may be found in Research Disclosure 37254, part 2 (1995), page 286.

Details of suitable silver halide emulsions, the production, ripening, stabilisation and spectral sensitisation thereof, including suitable spectral sensitisers, may be found in Research Disclosure 37254, part 3 (1995), page 286 and in Research Disclosure 37038, part XV (1995), page 89.

Photographic materials with camera sensitivity conventionally contain silver bromide-iodide emulsions, which may optionally also contain small proportions of silver chloride. Photographic print materials contain either silver chloride-bromide emulsions with up to 80 wt. % of AgBr or silver chloride-bromide emulsions with above 95 mol. % of AgCl.

Details relating to colour couplers may be found in Research Disclosure 37254, part 4 (1995), page 288 and in Research Disclosure 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in Research Disclosure 37254, part 5 (1995), page 290 and in Research Disclosure 37038, part XV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as fine droplets (0.05 to 0.8 $\mu$m in diameter) in the layers.

Suitable high-boiling organic solvents, methods for the introduction thereof into the layers of a photographic material and further methods for introducing chemical compounds into photographic layers may be found in Research Disclosure 37254, part 6 (1995), page 292.

The non-photosensitive interlayers generally located between layers of different spectral sensitivity may contain agents which prevent an undesirable diffusion of developer oxidation products from one photosensitive layer into another photo-sensitive layer with a different spectral sensitisation.

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers (latices), biocides and others.

Suitable compounds may be found in Research Disclosure 37254, part 8 (1995), page 292 and in Research Disclosure 37038, parts IV, V, VI, VII, X, M and XI (1995), pages 84 et seq..

The layers of colour photographic materials are conventionally hardened, i.e. the binder used, preferably gelatine, is crosslinked by appropriate chemical methods.

Suitable hardener substances may be found in Research Disclosure 37254, part 9 (1995), page 294 and in Research Disclosure 37038, part XII (1995), page 86.

Once exposed with an image, colour photographic materials are processed using different processes depending upon their nature. Details relating to processing methods and the necessary chemicals are disclosed in Research Disclosure 37254, part 10 (1995), page 294 and in Research Disclosure 37038, parts XVI to XXIII (1995), pages 95 et seq. together with example materials.

EXAMPLE 1

A colour photographic recording material for colour negative development was produced (material 1.1) by applying the following layers in the stated sequence onto a transparent cellulose triacetate film base of a thickness of 120 $\mu$m provided with an adhesion layer. Quantities are stated in g/m². The quantity of silver applied is stated as the corresponding quantities of $AgNO_3$. All the silver halides were stabilised with 0.1 g of 4-hydroxy-6-methyl-1,3,3a,7-tetraazaindene per 100 g of $AgNO_3$. The silver halide emulsions are characterised by their halide composition and, with regard to grain size, by the volume-weighted average particle diameter $\bar{d}_v$, which is calculated in accordance with the formula $$\bar{d}_v = \frac{\sum n_i \cdot d_i^4}{\sum n_i \cdot d_i^3}$$

wherein $n_i$ means the number of particles in the range i and $d_i$ means the diameter of spheres of an identical volume for the particles in the range i. $\bar{d}_v$ is stated below in $\mu$m.

Material 1.1

| Layer 1: | (anti-halo layer) | |
| | Gelatine | 0.80 |
| | Black colloidal silver | 0.28 |
| | UV absorber XUV-1 | 0.20 |
| Layer 2: | (low-sensitivity red-sensitivity layer) | |
| | Red-sensitised silver bromide-iodide-chloride emulsion (2.4 mol. % iodide; 10.5 mol. % chloride; $\bar{d}_v$ = 0.35) | 0.85 |
| | Gelatine | 0.60 |
| | Cyan coupler XC-1 | 0.30 |
| | Colored coupler XCR-1 | $2.0 \times 10^{-2}$ |
| | Colored coupler XCY-1 | $1.0 \times 10^{-2}$ |
| | DIR-coupler XDIR-1 | $1.0 \times 10^{-2}$ |
| Layer 3: | (medium-sensitivity red-sensitised layer) | |
| | Red-sensitised silver bromide-iodide emulsion (10.0 mol % iodide; $\bar{d}_v$ = 0.56) | 1.20 |
| | Gelatine | 0.90 |
| | Cyan coupler XC-1 | 0.20 |
| | Colored coupler XCR-1 | $7.0 \times 10^{-2}$ |
| | Colored coupler XCY-1 | $3.0 \times 10^{-2}$ |
| | DIR coupler XDIR-1 | $4.0 \times 10^{-3}$ |
| Layer 4: | (high-sensitivity red-sensitised layer)) | |
| | Red-sensitised silver bromide-iodide emulsion (6.8 mol. % iodide; $\bar{d}_v$ = 1.2) | 1.60 |
| | Gelatine | 1.20 |
| | Cyan coupler XC-2 | 0.15 |
| | DIR coupler XDIR-3 | $3.0 \times 10^{-2}$ |
| Layer 5: | (interlayer) | |
| | Gelatine | 1.00 |
| | Dye XF-1 | 0.10 |
| Layer 6: | (low-sensitivity green-sensitised layer) | |
| | Green-sensitised silver bromide-iodide-chloride emulsion (9.5 mol % iodide; 10.4 mol % chloride; $\bar{d}_v$ = 0.5 $\mu$m) | 0.66 |
| | Gelatine | 0.90 |
| | Magenta coupler M-1 | 0.30 |
| | Colored coupler XMY-1 | $2.0 \times 10^{-2}$ |
| | DIR coupler XDIR-1 | $5.0 \times 10^{-3}$ |
| | DIR coupler XDIR-2 | $1.0 \times 10^{-3}$ |
| Layer 7: | (medium-sensitivity green-sensitised layer) | |
| | Green-sensitised silver bromide-odide emulsion 10.0 mol % iodide; $\bar{d}_v$ = 0.56 $\mu$m) | 1.40 |
| | Gelatine | 0.90 |
| | Magenta coupler M-1 | 0.24 |
| | Colored coupler XMY-l | $4.0 \times 10^{-2}$ |
| | DIR coupler XDIR-1 | $5.0 \times 10^{-3}$ |
| | DIR coupler XDIR-2 | $3.0 \times 10^{-3}$ |
| Layer 8: | (high-sensitivity green-sensitised layer)) | |
| | Green-sensitised silver bromide-iodide emulsion (6.8 mol % iodide; $\bar{d}_v$ = 1.1 $\mu$m) | 1.70 |
| | Gelatine | 1.20 |
| | Magenta coupler M-1 | $3.0 \times 10^{-2}$ |
| | Colored coupler XMY-2 | $5.0 \times 10^{-2}$ |
| | DIR coupler XDIR-3 | $5.0 \times 10^{-2}$ |
| Layer 9: | (interlayer) | |
| | Gelatine | 0.40 |
| | Polyvinylpyrrolidone | $1.0 \times 10^{-2}$ |
| Layer 10: | (yellow filter layer)) | |
| | Gelatine | 0.80 |
| | Yellow colloidal silver sol (silver filter yellow), Ag | 0.10 |
| Layer 11: | (low-sensitivity blue-sensitised layer) | |
| | Blue-sensitised silver bromide-odide-chloride emulsion (6.0 mol % iodide; 10.4 mol % chloride; $\bar{d}_v$ = 0.78 $\mu$m) | 0.40 |
| | Gelatine | 1.00 |

-continued

| | | |
|---|---|---|
| | Yellow coupler XY-1 | 0.40 |
| | DIR coupler XDIR-1 | $3.0 \times 10^{-2}$ |
| Layer 12: | (medium-sensitivity blue-sensitised layer)) | |
| | Blue-sensitised silver bromide-iodide-chloride emulsion (8.8 mol % iodide; 15.0 mol % chloride; $\overline{d}_v = 0.77 \mu m$) | 0.12 |
| | (12.0 mol % iodide; 15.0 mol % chloride; $\overline{d}_v = 1.0 \mu m$) | 0.28 |
| | Gelatine | 0.77 |
| | Yellow coupler XY-1 | 0.58 |
| Layer 13: | (high-sensitivity blue-sensitised layer)) | |
| | Blue-sensitised bromide-odide emulsion (12.0 mol % iodide; $\overline{d}_v = 1.2 \mu m$) | 1.20 |
| | Gelatine | 0.90 |
| | Yellow coupler XY-1 | 0.10 |
| | DIR coupler XDIR-3 | $2.0 \times 10^{-2}$ |

-continued

| | | |
|---|---|---|
| Layer 14: | (protective layer) | |
| | Micrate silver bromide-iodide emulsion (4.0 mol % iodide; $\overline{d}_v = 0.05$) | 0.25 |
| | Gelatine | 1.40 |
| | UV absorber XUV-1 | 0.30 |
| | UV absorber XUV-2 | 0.20 |
| Layer 16: | (hardening layer) | |
| | Gelatine | 0.20 |
| | Hardener XH-1 | 0.86 |
| | Persoftal | 0.04 |

Compounds used in material 1.1:

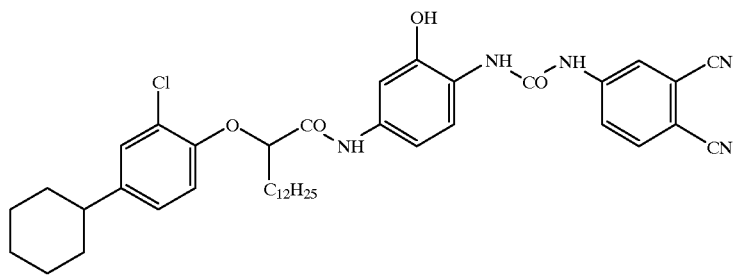

XC-1

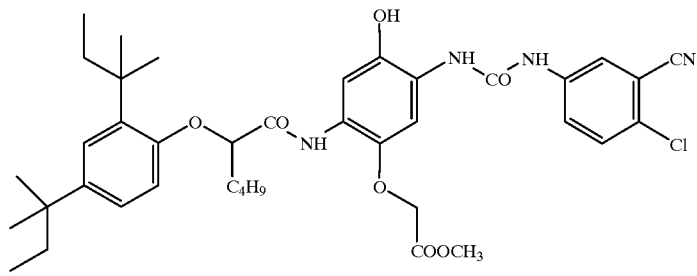

XC-2

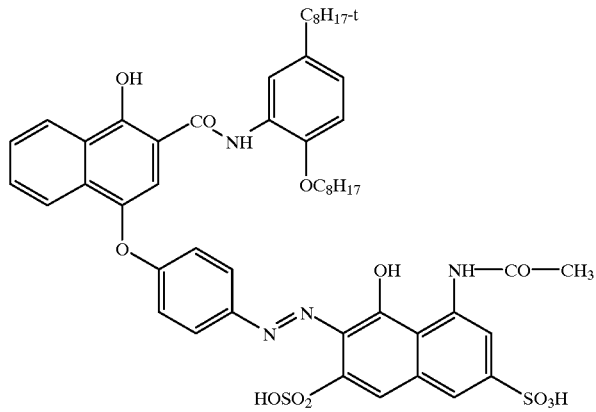

XCR-1

XCY-1
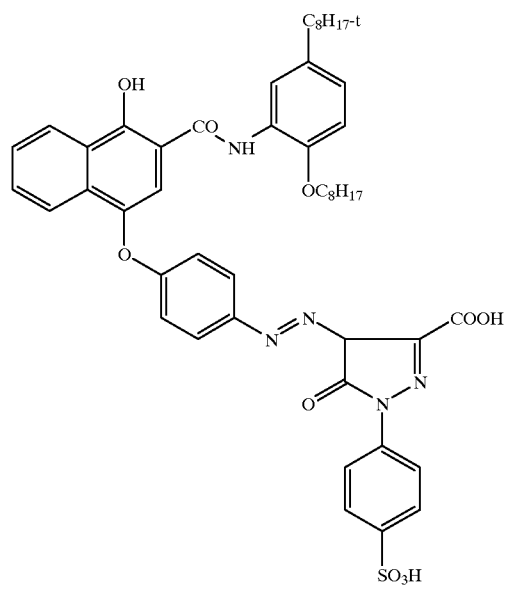
XMY-1
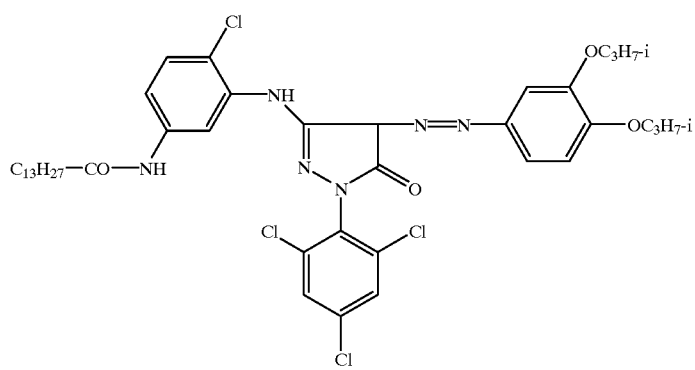
XMY-2
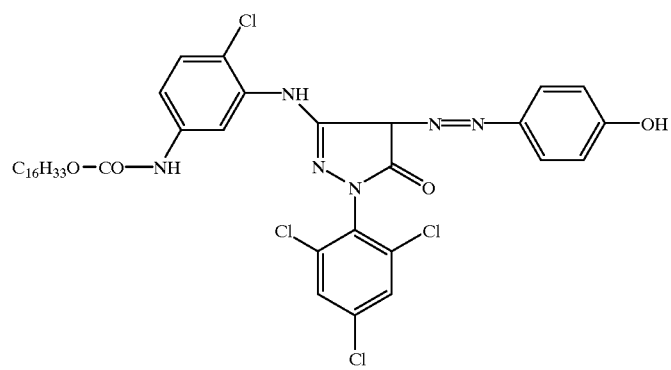
XY-1
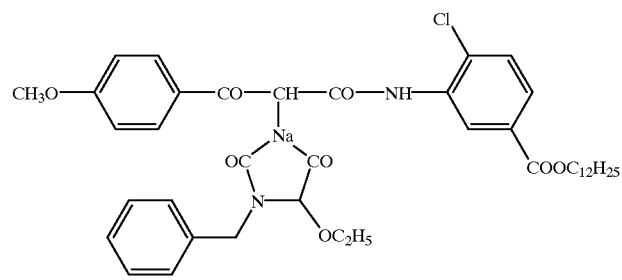

XDIR-1
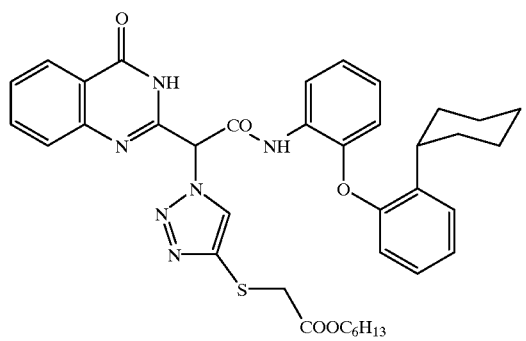
XDIR-2
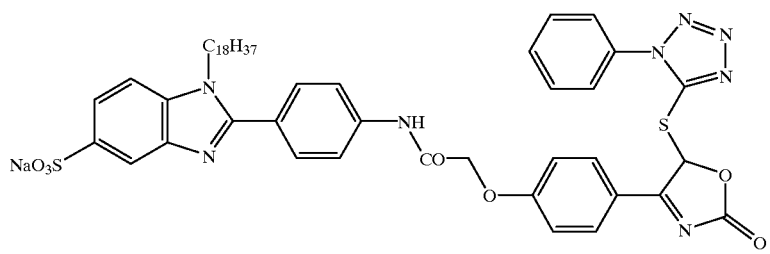
XDIR-3
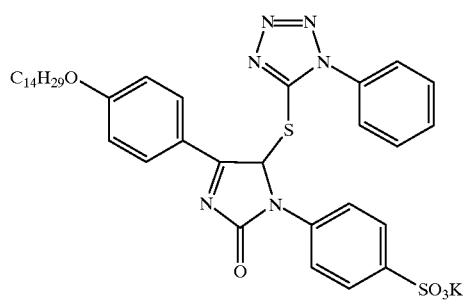
XF-1
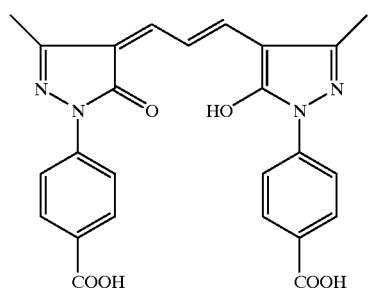
XUV-1
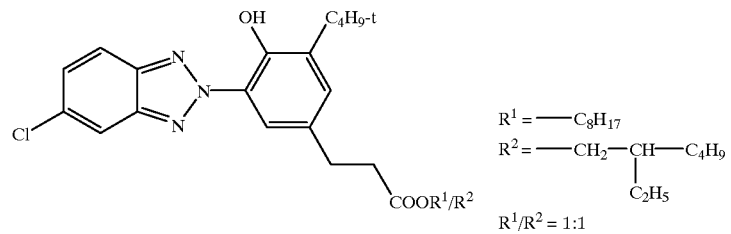

XUV-2

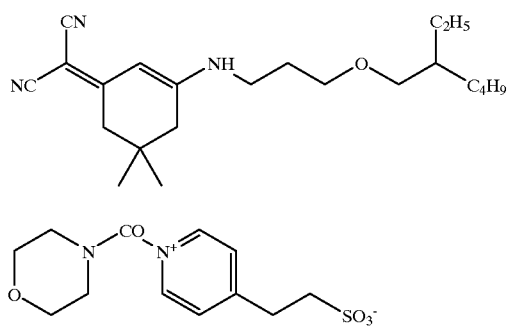

XH-1

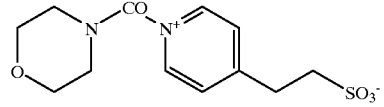

The colourless and coloured couplers were each incorporated together with the same quantity of tricresyl phosphate using known emulsifying methods. The compounds of the combination according to the invention, i.e. the 2-equivalent pyrazolone coupler and the white coupler of the formula I, were also incorporated in this manner as described below.

General procedure for emulsifying the compounds according to the invention of the formula I 10 g of compound according to the invention of the formula I were dissolved together with 10 g of TCP and 30 g of ethyl acetate and emulsified in a high speed mixer at 50° C. into 100 g of a 10% gelatine solution, to which 0.05 g of Erkantol® (wetting agent) had been added. The ethyl acetate was then stripped out under a vacuum. The still liquid dispersion was then solidified at 6° C.

Materials 1.2 to 1.5 differ from material 1.1 in that, as may be seen from Table 1, 0.125 mol of a compound of the formula I was additionally incorporated into layer 10. Materials 1.6 and 1.7 contained a known white coupler (compounds A and B respectively) instead of the compound according to the invention of the formula I. Two test strips of each of materials 1.1 to 1.7 received a graduated white exposure and a further test strip received a selective graduated blue exposure. All the test strips were then processed using the process described by E. Ch. Gehret in The British J. of Photography, 1974, page 597. The colour separation of each of the various materials was determined from the blue-exposed and the white-exposed samples. One of the white-exposed and developed samples was then stored at normal room temperature ($t_z$) and the other for 3 days at 60° C. and 90% relative humidity. Magenta density at point E+log H was then measured on the sample stored at room temperature (E was measured at $D_{min}$+0.2). The density of the sample exposed to the different climatic conditions was measured at the same point. The difference $\Delta D = D_{clim.} - D_{tz}$ was then calculated. The magenta minimum density ($D_{min/magenta/tz}$) of the sample stored at room temperature was also determined.

TABLE 1

| Material | Additional compound in layer 10 | Blue/green colour separation log H | $D_{min/magenta/tz}$ | $D_{clim.} - D_{tz}$ (at E + log H) | |
|---|---|---|---|---|---|
| 1.1 | — | 0.8 | 0.61 | 0.23 | Comparison |
| 1.2 | I-3 | 1.2 | 0.48 | 0.20 | Invention |
| 1.3 | I-4 | 1.3 | 0.51 | 0.21 | Invention |
| 1.4 | I-7 | 1.2 | 0.51 | 0.23 | Invention |
| 1.5 | I-13 | 1.1 | 0.49 | 0.23 | Invention |
| 1.6 | Compound A | 1.1 | 0.50 | 0.68 | Comparison |
| 1.7 | Compound B | 1.2 | 0.51 | 0.83 | Comparison |

Compound A:

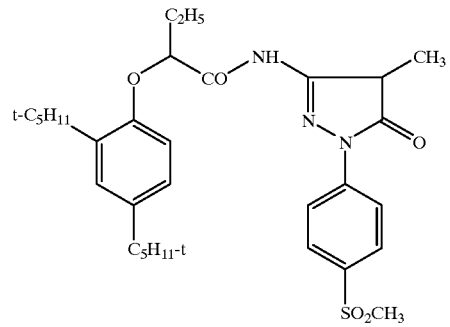

TABLE 1-continued

| Material | Additional compound in layer 10 | Blue/green colour separation log H | $D_{min/magenta/tz}$ | $D_{clim.} - D_{tz}$ (at E + log H) |
|---|---|---|---|---|

Compound B:

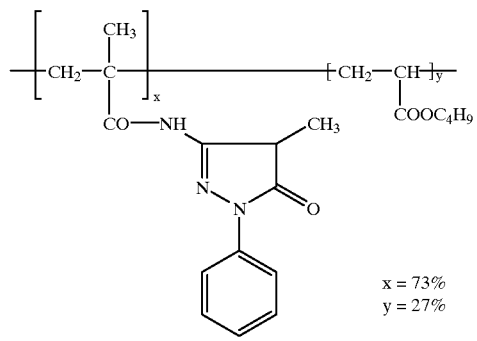

x = 73%
y = 27%

It is clearly evident from the results of Table 1 that the compounds according to the invention distinctly reduce magenta fog without increasing the difference ($D_{clim.}-D_{tz}$) and they distinctly increase blue/green separation. The difference ($D_{clim.}-D_{tz}$) is a measure of the stability of the developed image as it is possible to use it to make statements as to changing print conditions during storage of the developed colour negative image.

EXAMPLE 2

The same method was used as in Example 1, except that magenta coupler M-4 was used instead of magenta coupler M-1 in layers 6, 7 and 8 of material 1.1. A further 10 mol. % of compound I-3, relative to the magenta coupler in layers 6, 7 and 8, were then additionally added in material 2.2. Further test examples and the associated combinations may be found in Table 2. White couplers (C, D), which do not fall within the combination according to the invention, were used in addition to the combinations according to the invention.

TABLE 2

| Material | Magenta-coupler in layers 6, 7 & 8 | White coupler in layers 6,7 & 8 | Sensitivity (rel.) | $D_{min}/magenta$ | $D_{clim.} - D_{tz}$ (at E + log H) | |
|---|---|---|---|---|---|---|
| 2.1 | M-4 | — | 100 | 0.68 | 0.23 | Comparison |
| 2.2 | " | I-4 | 120 | 0.48 | 0.22 | Invention |
| 2.3 | " | Cmpnd. C | 125 | 0.47 | 0.72 | Comparison |
| 2.4 | M-9 | — | 105 | 0.70 | 0.24 | Comparison |
| 2.5 | " | I-8 | 128 | 0.47 | 0.24 | Invention |
| 2.6 | " | Cmpnd. D | 128 | 0.49 | 0.84 | Comparison |
| 2.7 | M-16 | — | 101 | 0.72 | 0.22 | Comparison |
| 2.8 | " | I-13 | 125 | 0.48 | 0.22 | Invention |
| 2.9 | M-15 | — | 100 | 0.71 | 0.23 | Comparison |
| 2.10 | " | I-14 | 117 | 0.50 | 0.24 | Invention |

As is clearly evident from Table 2, the combinations according to the invention have a lower $D_{min/magenta}$ combined with higher sensitivity. While an increase in sensitivity combined with a low $D_{min/magenta}$ may indeed also be observed in the combinations with white couplers C and D, these combinations exhibit poor storage stability, as is clear from the difference $\Delta D = D_{clim.} - D_{tz}$.

The following white couplers were used by way of comparison in Example 2:

Compound C:

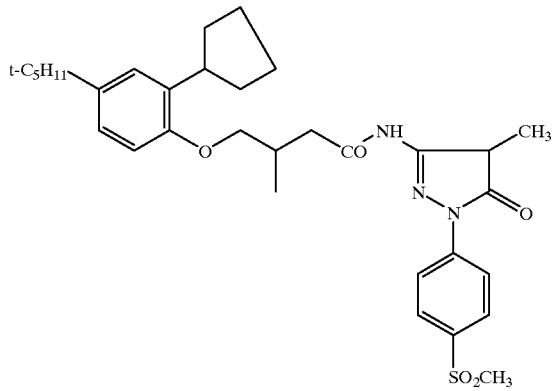

Compound D:

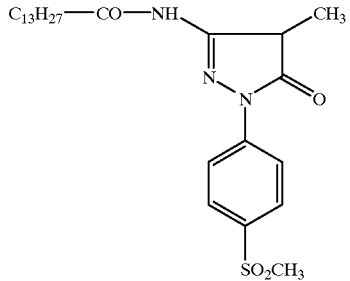

We claim:

1. A color photographic recording material which comprises at least one red-sensitive silver halide emulsion layer which is associated with a cyan coupler, at least one green-sensitive silver halide emulsion layer which is associated with a magenta coupler, at least one blue-sensitive silver halide emulsion layer which is associated with a yellow coupler and optionally further non-photosensitive layers, wherein at least one green-sensitive silver halide emulsion layer contains a 2-equivalent pyrazolone coupler and that at least one photosensitive or non-photosensitive layer contains a compound of the formula (I)

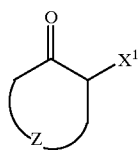
(I)

in which
X$^1$ is an acyl residue derived from an aliphatic, cycloaliphatic or aromatic carboxylic or sulphonic acid, a carbonic acid semi-ester or a carbamic acid,
Z is the residue required to complete a saturated or partially unsaturated 5- or 6-membered carbocyclic ring which is optionally substituted and/or provided with a further fused ring or ring system.

2. The recording material according to claim 1, wherein the 2-equivalent pyrazolone coupler is of the formula II

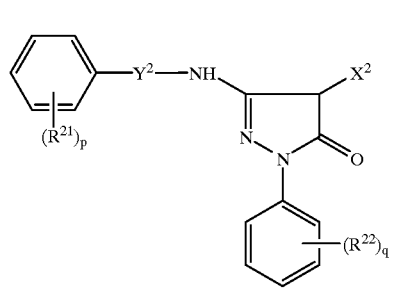
(II)

in which
R$^{21}$ is fluorine, chlorine, bromine, cyano, —NO$_2$, —CF$_3$, alkyl, aryl, acyl, silyl, alkoxy, acylamino, sulphonamido, alkylsulphonyl or arylsulphonyl;
R$^{22}$ is fluorine, chlorine, bromine, cyano, —NO$_2$, —CF$_3$, alkyl, acyl, alkoxy, acylamino, sulphonamido, alkylsulphonyl, arylsulphonyl, alkoxysulphonyl or aryloxysulphonyl;
X$^2$ is a leaving group;
Y$^2$ is a single chemical bond or —CO—;
p and q (mutually independently): are 0 (zero) or an integer from 1 to 5, wherein if a or b is >1, the substitutents R$^{21}$ or R$^{22}$ are identical or different.

3. The recording material according to claim 2, wherein the 2-equivalent pyrazolone coupler is of the formula III

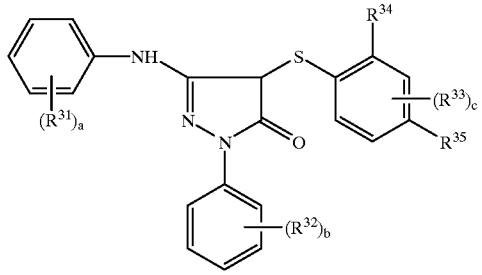

in which
R$^{31}$ is fluorine, chlorine, bromine, cyano, —NO$_2$, —CF$_3$, alkyl, aryl, acyl, silyl, alkoxy, acylamino, sulphonamido, alkylsulphonyl or arylsulphonyl;
R$^{32}$ is fluorine, chlorine, bromine, cyano, —NO$_2$, —CF$_3$, alkyl, acyl, alkoxy, acylamino, sulphonamido, alkylsulphonyl, arylsulphonyl, alkoxysulphonyl or aryloxysulphonyl;
R$^{33}$ is fluorine, chlorine, bromine, cyano, alkyl, aryl, acyl, silyl, alkylsulphonyl or arylsulphonyl;
R$^{34}$ and R$^{35}$ independently of one another are hydrogen, cyano, alkyl, alkoxy, acylamino, sulphonamido, alkoxycarbonyl, alkylsulphonyl, arylsulphonyl, alkoxysulphonyl or aryloxysulphonyl, providing that either R$^{34}$ or R$^{35}$ denotes hydrogen;
a and b (mutually independently): are 0 (zero) or an integer from 1 to 5, wherein if a or b is >1, substitutents R$^{31}$ or R$^{32}$ are identical or different;
c is 0 (zero) or an integer from 1 to 4, wherein two or more substituents R$^{33}$ are identical or different.

4. The recording material according to claim 3, wherein the 2-equivalent pyrazolone coupler is of the formula IV

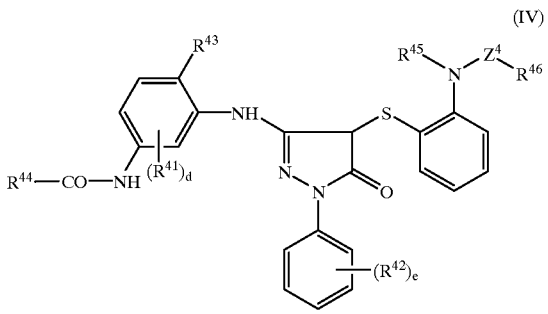
(IV)

in which
R$^{41}$ fluorine, chlorine, bromine, cyano, —NO$_2$, —CF$_3$, alkyl, aryl, acyl, silyl, alkoxy, acylamino, sulphonamido, alkylsulphonyl or arylsulphonyl:
R$^{42}$ is fluorine, chlorine, bromine, cyano, —NO$_2$, —CF$_3$, alkyl, acyl, alkoxy, acylamino, sulphonamido, alkylsulphonyl, arylsulphonyl, alkoxysulphonyl or aryloxysulphonyl;
R$^{43}$ is chlorine or alkoxy;
R$^{44}$ is alkyl or alkoxy;
R$^{45}$ is hydrogen, alkyl or aryl;
R$^{46}$ is alkyl or aryl;
Z$^4$ is —CO— or —SO$_2$—;
d is 0 or 1; and
e is an integer from 3 to 5, wherein two or more substituents R$^{42}$ are identical or different.

5. The recording material according to claim 1, wherein X$^1$ is a group of the formula —CONH—R$^{11}$, in which R$^{11}$ is alkyl, cycloalkyl or aryl.

6. The recording material according to claim 1, wherein X$^1$ is —CO—R$^{11}$, —COOR$^{11}$, —CONH—R$^{11}$, —CONR$^{11}$—R$^{12}$ or —SO$_2$—R$^{11}$, in which R$^{11}$ and R$^{12}$ independently of one another are alkyl cycloalkyl, aryl or hetaryl.

7. The recording material according to claim 1, wherein the compound of formula 1 is selected from the group consisting of

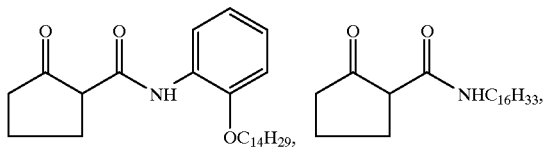
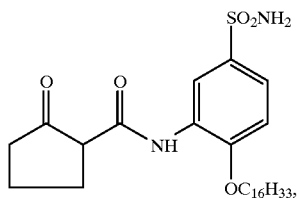
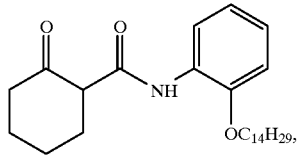
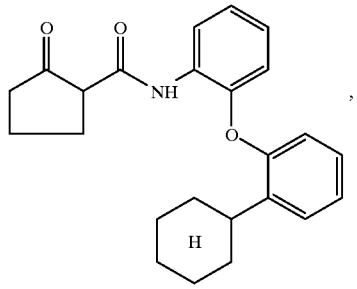
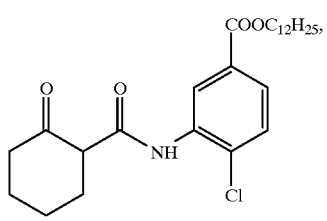
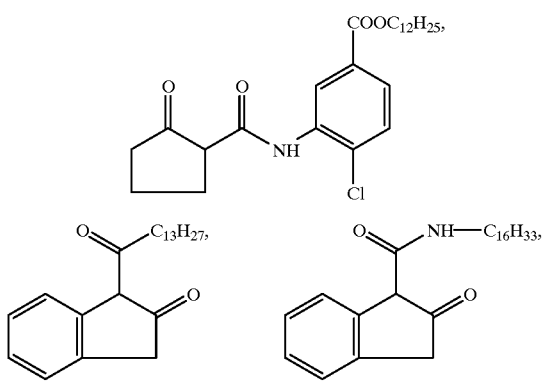
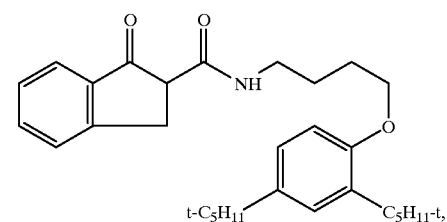

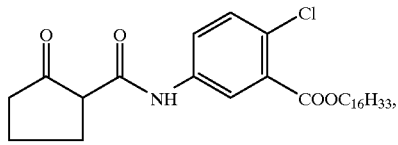
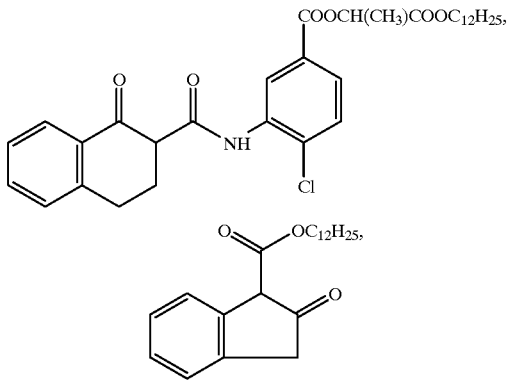
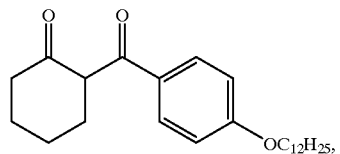
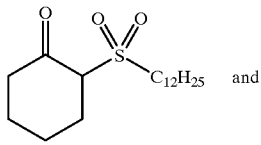
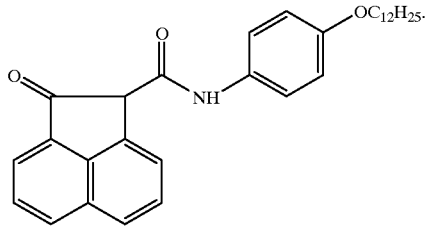

and

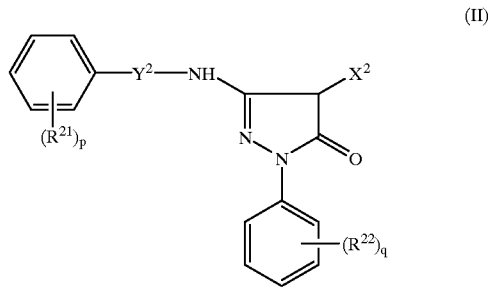

8. The recording material according to claim 7, wherein the 2-equivalent pyrazolone coupler is of the formula II (II)

in which
 $R^{21}$ is fluorine, chlorine, bromine, cyano, —$NO_2$, —$CF_3$, alkyl, aryl, acyl, silyl, alkoxy, acylamino, sulphonamido, alkylsulphonyl or arylsulphonyl;
 $R^{22}$ is fluorine, chlorine, bromine, cyano, —$NO_2$, —$CF_3$, alkyl, acyl, alkoxy, acylamino, sulphonamido, alkylsulphonyl, arylsulphonyl, alkoxysulphonyl or aryloxysulphonyl;

$X^2$ is a leaving group;

$Y^2$ is a single chemical bond or —CO—;

a and b (mutually independently): are 0 (zero) or an integer from 1 to 5, wherein if a or b is >1, the substitutents $R^{21}$ or $R^{22}$ are identical or different.

9. The recording material according to claim 7, wherein the 2-equivalent pyrazolone coupler is of the formula III

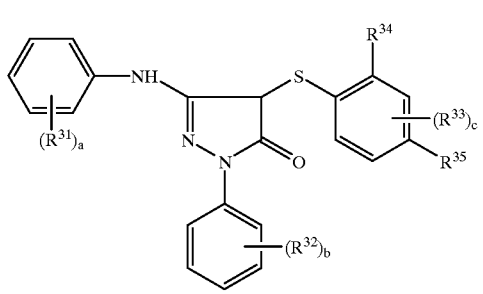

(III)

in which $R^{31}$ is fluorine, chlorine, bromine, cyano, —NO$_2$, —CF$_3$, alkyl, aryl, acyl, silyl, alkoxy, acylamino, sulphonamido, alkylsulphonyl or arylsulphonyl;

$R^{32}$ is fluorine, chlorine, bromine, cyano, —NO$_2$, —CF$_3$, alkyl, acyl, alkoxy, acylamino, sulphonamido, alkysulphonyl, arylsulphonyl, alkoxysulphonyl or aryloxysulphonyl;

$R^{33}$ is fluorine, chlorine, bromine, cyano, alkyl, aryl, acyl, silyl, alkylsulphonyl or arylsulphonyl;

$R^{34}$ and $R^{35}$ independently of one another are hydrogen, cyano, alkyl, alkoxy, acylamino, sulphonamido, alkoxycarbonyl, alkylsulphonyl, arylsulphonyl, alkoxysulphonyl or aryloxysulphonyl, providing that either $R^{34}$ or $R^{35}$ denotes hydrogen;

a and b (mutually independently): are 0 (zero) or an integer from 1 to 5, wherein if a or b is >1, substitutents $R^{31}$ or $R^{32}$ are identical or different;

c is 0 (zero) or an integer from 1 to 4, wherein two or more substituents $R^{33}$ are identical or different.

10. The recording material according to claim 7, wherein the 2-equivalent pyrazolone coupler is of the formula IV

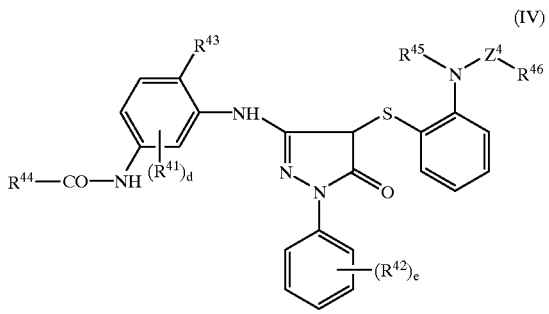

(IV)

in which $R^{41}$ is fluorine, chlorine, bromine, cyano, —NO$_2$, —CF$_3$, alkyl, aryl, acyl, silyl, alkoxy, acylamino, sulphonamido, alkylsulphonyl or arylsulphonyl;

$R^{42}$ is fluorine, chlorine, bromine, cyano, —NO$_2$, —CF$_3$, alkyl, acyl, alkoxy, acylamino, sulphonamido, alkylsulphonyl, arylsulphonyl, alkoxysulphonyl or aryloxysulphonyl;

$R^{43}$ is chlorine or alkoxy;

$R^{44}$ is hydrogen, alkyl or aryl;

$R^{46}$ is alkyl or aryl;

$Z^4$ is —CO— or —SO$_2$—;

d is 0 or 1; and e is an integer from 3 to 5, wherein two or more substituents $R^{42}$ are identical or different.

* * * * *